US008012724B2

(12) United States Patent
Holm et al.

(10) Patent No.: US 8,012,724 B2
(45) Date of Patent: Sep. 6, 2011

(54) PRODUCTION OF DEGUMMED FATTY ACID ALKYL ESTERS USING BOTH LIPASE AND PHOSPHOLIPASE IN A REACTION MIXTURE

(75) Inventors: Hans Christian Holm, Hellerup (DK); Per Munk Nielsen, Hillerod (DK); Morten Wurtz Christensen, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 796 days.

(21) Appl. No.: 11/916,052

(22) PCT Filed: Jun. 13, 2006

(86) PCT No.: PCT/DK2006/000329
§ 371 (c)(1),
(2), (4) Date: Nov. 30, 2007

(87) PCT Pub. No.: WO2006/133698
PCT Pub. Date: Dec. 21, 2006

(65) Prior Publication Data
US 2008/0199924 A1  Aug. 21, 2008

Related U.S. Application Data

(60) Provisional application No. 60/690,431, filed on Jun. 14, 2005.

(30) Foreign Application Priority Data

Jun. 13, 2005 (DK) .................................. 2005 00858

(51) Int. Cl.
C12P 7/62 (2006.01)
(52) U.S. Cl. ........................................................ 435/135
(58) Field of Classification Search .................. None
See application file for complete search history.

(56) References Cited

U.S. PATENT DOCUMENTS

| 5,264,367 | A | | 11/1993 | Aalrust et al. | |
|---|---|---|---|---|---|
| 5,827,719 | A | | 10/1998 | Sandal et al. | |
| 5,989,599 | A | * | 11/1999 | Chmiel et al. | 426/33 |
| 2004/0251209 | A1 | | 12/2004 | Copeland | |

FOREIGN PATENT DOCUMENTS

| CN | 1442472 A | 9/2003 |
|---|---|---|
| CN | 1453332 A | 11/2003 |
| EP | 0 622 446 | 11/1994 |
| JP | 02/153991 * | 6/1990 |
| JP | 2153997 | 6/1990 |
| WO | WO 88/02775 | 4/1988 |
| WO | WO/98/26057 A1 | 6/1998 |
| WO | WO/00/32758 A1 | 6/2000 |
| WO | WO/00/60063 A1 | 10/2000 |
| WO | WO 01/83770 | 11/2001 |
| WO | WO/01/83770 A2 | 11/2001 |
| WO | WO 03/100044 A1 | 12/2003 |
| WO | WO 2004/064987 A2 | 8/2004 |
| WO | WO/2006/008508 A1 | 1/2006 |

OTHER PUBLICATIONS

Clausen et al. Dansk Kemi, vol. 83, No. 2, pp. 24-27 (2002).
Xu et al., Biotechnology Letters, vol. 25, pp. 1239-1241 (2003).
Kolattukudy et al, "Lipases", Ed. Borgstrom and Brockman, Elsevier 4984, pp. 471-504 (1984).
Kaieda et al., Journal of Bioscience and Bioengineering, vol. 91, No. 1, pp. 12-15 (2001).
Du et al., Biotechnol Appl. Biochem., vol. 38, pp. 103-106 (2003).
Shimada et al., Journal of Molecular Catalysis, vol. 17, pp. 133-142 (2002).
Xu et al., Biocatalysis and Biotransformation, vol. 22, No. 1, pp. 45-48 (2004).
Boutur et al., Journal of Biotechnology, vol. 42, pp. 23-33 (1995).
Boschish et al., Fats and Oils Handdbook, AOCS Press, pp. 428-433 (1998).
Clausen, Eur. J. Lipid. Sci. Technol., vol. 103, pp. 333-340 (2001).
Bailey's Industrial Oil and Fat Prod, ch 2+ 7, pp. 51-121 + 285-339 (2005).
Jorn Borch Soe Declaration, 3 pages (Feb. 28, 2011).
Lai et al, J Chem Technol Biotechnol, vol. 80, pp. 331-337 (2005).
Sarney et al, Dep Biol Enz JAOCS, vol. 71, No. 1, pp. 93-96 (1994).
Song et al, Biochim et Biophys Acta, vol. 1547, pp. 370-378 (2001).
Soy Bean Oil, case No. 8001-22-7, Wako Pure Chemical Industries Ltd (Feb. 7, 2010).
Wu, Journal of the Chinese Cereals and Oils Association, vol. 19, No. 2, pp. 79-81 (2004).
EP 1 893 764 B1, 2 pages (Jan. 7, 2009).
Priority Document for GB 0416035.4, 108 pages (Jul. 16, 2004).

* cited by examiner

*Primary Examiner* — Sandra Saucier
(74) *Attorney, Agent, or Firm* — Kristin J. McNamara

(57) ABSTRACT

The present invention relates to a method for producing fatty acid alkyl esters, such as fatty acid methyl esters (FAME) and fatty acid ethyl esters with a low level of impurities such as phospholipids. The method of the invention is simplified by combining two process steps into one single process step and is therefore economically cheaper. The method includes mixing water, alcohol, triglyceride and/or free fatty acids a lipolytic enzyme and a phospholipase. Subsequently the aqueous phase, which contains glycerine, residual enzyme and most of the hydrolyzed phospholipids, is separated from the non-aqueous phase, whereby the content of phospholipids in the non-aqueous phase is reduced.

17 Claims, No Drawings

PRODUCTION OF DEGUMMED FATTY ACID ALKYL ESTERS USING BOTH LIPASE AND PHOSPHOLIPASE IN A REACTION MIXTURE

CROSS-REFERENCE TO RELATED APPLICATIONS

This application is a 35 U.S.C. 371 national application of PCT/DK2006/000329 filed Jun. 13, 2006, which claims priority or the benefit under 35 U.S.C. 119 of Danish application no PA 2005 00858 filed Jun. 13, 2005 and U.S. provisional application No. 60/690,431 filed Jun. 14, 2005, the contents of which are fully incorporated herein by reference.

FIELD OF THE INVENTION

The present invention relates to a simplified method for producing degummed fatty acid alkyl esters i.e. fatty acid alkyl esters wherein the content of impurities such as phospholipids has been reduced. The method comprises conversion of fats and oils to fatty acid alkyl esters by use of one or more lipolytic enzymes and one or more phospholipases in one solution.

BACKGROUND ART

Biodiesel, generally classified as alkyl esters of fatty carboxylic acid originated from vegetable or animal fats and oils, has become more attractive recently because of its environmental benefits. Although biodiesel is at present successfully produced chemically by transesterification (using e.g. NaOH and/or sodium methoxide as catalyst), there are several associated problems to restrict its development, such as pre-processing of oil due to high contents of free fatty acids, removal of the chemical catalyst from the ester and glycerol phase, removal of inorganic salts during glycerol recovery and reduction of the content of phospholipids prior to the transesterification step.

The disadvantages caused by chemical catalysts are largely prevented by using lipolytic enzymes as the catalysts and in recent years interest has developed in the use of lipases with or without immobilization in transesterification for the production of biodiesel.

Fungal esterases may be used in the enzymatic production of esters, where they may replace catalysts like mineral acid (e.g. sulphuric acid, hydrogen chloride, and chlorosulfonic acid), amphoteric hydroxides of metals of groups I, II, III, and IV, and others. The use of enzymes for ester synthesis has been described in the prior art, in particular enzymes classified in EC 3.1.1 Carboxylic ester hydrolases according to Enzyme Nomenclature (Recommendations of the Nomenclature Committee of the International Union of Biochemistry and Molecular Biology, 1992 or later).

WO 88/02775 discloses lipases A and B from *Candida antarctica*. It states that *C. antarctica* lipase B (CALB) is more effective for ester synthesis.

Cutinases are lipolytic enzymes capable of hydrolyzing the substrate cutin. Cutinases are known from various fungi (P. E. Kolattukudy in "Lipases", Ed. B. Borgström and H. L. Brockman, Elsevier 1984, 471-504). The amino acid sequence of a cutinase from Humicola insolens has been published (U.S. Pat. No. 5,827,719).

Many researchers have reported that a high yield of alkyl esters could be reached in the presence of organic solvents, but because of the toxicity and flammability of organic solvents lipase-catalysed alcoholysis in a solvent-free medium is more desirable. Methanolysis catalysed by lipases has been shown to take place in a water-containing system free of organic solvents. In such systems lipases which are less sensitive to methanol is advantageous (Kaieda et al. J. Biosci. Bioeng. 2001, 91:12-15). It is well known that excessive short-chain alcohols such as methanol might inactivate lipase seriously. However, at least three molar equivalents of methanol are required for the complete conversion of the oil to its corresponding methyl ester. Du et al. (Biotechnol. Appl. Biochem. 2003, 38:103-106) studied the effect of molar ratio of oil/methanol comparatively during non-continuous batch and continuous batch operation.

To avoid inactivation of the lipases the methanol concentration has been kept low by step-wise addition of methanol throughout the reaction (Shimada et al. J Mol. Catalysis Enzymatic, 2002, 17:133-142; Xu et al. 2004, Biocat. Biotransform. 22:45-48).

Fungal lipases as defined in EC 3.1.1.3 may be used in alcoholysis of triglycerides and replace alkaline chemicals catalysts such as sodium methoxide or potassium hydroxide. Boutur et al. (J. Biotechnol. 1995, 42:23-33) reported a lipase from *Candida deformans* which were able to catalyse both alcoholysis of triglyceride (TG) and esterification of free fatty acids (FFA), but not under the same reaction conditions. Under the conditions described by Boutur et al. only the esterification was catalysed.

In order to obtain a more economic production of fatty acid alkyl esters for biodiesel, there is a need for a simpler and integrated process, resulting in faster conversion of fats and oils to their corresponding methyl or ethyl esters and a higher yield in said conversion and minimizing the capital investment needed for process units. Further, fats and oils obtained from the usual production processes by compressing oil-bearing materials or by extracting oil from the materials and removing the extraction solvent contain impurities such as polar lipids mainly composed of phospholipids, as well as fatty acids, pigments, odor components and the like. It is necessary to remove these impurities by a refining process, which may require a degumming step. Various physical and chemical methods are used to degum oil (as described by Bochisch, M. in Fats and Oils Handbook, AOCS Press, 1998, p. 428-433) In the art it is known to use phospholipase for enzymatic degumming of an edible oil (U.S. Pat. No. 5,264,367; JP-A-2153997; and EP 622446), to reduce the phosphorus content of said water degummed oils. Enzymatic degumming conditions are described by Clausen, K in Eur. J. Lipid Sci. Technol. 103 (2001), 333-340. The key steps are citric acid treatment, pH adjustment to app. 5.0, enzyme addition and mixing using a high shear mixer.

SUMMARY OF THE INVENTION

The present invention relates to a method for producing fatty acid alkyl esters, such as fatty acid methyl esters (FAME) and fatty acid ethyl esters with a low level of impurities such as phospholipids. The method of the invention is simplified by combining two process steps into one single process step and is therefore economically cheaper. The method includes mixing water, alcohol, triglyceride and/or free fatty acids, and one or more lipolytic enzymes and one or more phospholipases selected from the types $A_1$, $A_2$, B and lyso-phospholipases. Subsequently the aqueous phase, which contains glycerine, residual enzyme and most of the hydrolyzed phospholipids, is separated from the non-aqueous phase, whereby the content of phospholipids in the non-aqueous phase is reduced.

The combination of lipolytic enzymes and phospholipases in the same mixture allows a fast, simple and high yielding production of phosphorous reduced fatty acid alkyl esters from triglycerides and/or free fatty acids. The mixture of the method of the present invention has a relatively high alcohol concentration in the aqueous phase. This is advantageous for the transesterification performed by the lipases, as described above. In the prior art microbial phospholipases have been reported to be relatively unstable at high concentrations of organic solvents (see Song et al, Biochemica et Biophysica Acta, 1547 (2001) 370-378). Therefore it is surprising that the enzymatic degumming step (enzymatic hydrolysis of phospholipids by phospholipases) in the method of the present invention, takes place under the same conditions as the transesterification performed by the lipases.

Further, the invention relates to a batch process or a continuous, staged process to produce phosphorous reduced fatty acid alkyl esters using lipolytic enzymes and phospholipases as described above, wherein the alcohol is added continuously or stepwise, and wherein the enzymes are recycled or used only once. Also, the enzymes may be immobilised on silica beads or free in solution.

It is emphasised that the fatty acid alkyl esters produced by the method of the invention is not exclusively for biodiesel, but can also be used as basic oleochemical in further down stream processes in the oleochemical industry.

Phosphorous Reduced

The phrase "phosphorous reduced" means that the content of phosphorous containing components, such as phospholipids has been reduced. Non-hydratable phospholipids in the non-aqueous phase are being hydrolyzed by the phospholipase and converted into hydratable phospholipids, which is then extracted from the oil-phase into the aqueous phase. The content of phosphorous in the fatty phase is measured by the method described in Clausen, K in Eur. J. Lipid Sci. Technol. 103 (2001), 333-340. In accordance with the Example herein it is the P-value after 24 hours reaction time.

Accordingly, the phosphorous reduced fatty acid alkyl esters of the present invention contain not more than 500 ppm phosphorous, preferably not more than 200 ppm phosphorous, more preferably not more than 100 ppm phosphorous, more preferably not more than 75 ppm phosphorous, more preferably not more than 50 ppm phosphorous, more preferably not more than 40 ppm phosphorous, more preferably not more than 30 ppm phosphorous, more preferably not more than 25 ppm phosphorous, more preferably not more than 20 ppm phosphorous, more preferably not more than 15 ppm phosphorous, more preferably not more than 10 ppm phosphorous, even more preferably not more than 5 ppm phosphorous, most preferably not more than 1 ppm phosphorous.

DETAILED DESCRIPTION OF THE INVENTION

The present invention relates to a method for producing fatty acid alkyl esters, such as fatty acid methyl esters (FAME) and fatty acid ethyl esters with a low level of impurities such as phospholipids. The method of the invention is simplified by combining two process steps into one single process step and is therefore economically cheaper. The method includes mixing water, alcohol, triglyceride and/or free fatty acids, and one or more lipolytic enzymes and one or more phospholipases selected from the types $A_1$, $A_2$, B and lyso-phospholipases. Subsequently the aqueous phase, which contains glycerine, residual enzyme and most of the hydrolyzed phospholipids, is separated from the non-aqueous phase by settling, filtering or centrifuging, whereby the content of phospholipids in the non-aqueous phase is reduced.

Substrates Suitable substrates for production of fatty acid alkyl esters in accordance with the present invention are a broad variety of vegetable oils and fats; rapeseed and soybean oils are most commonly used, though other crops such as mustard, sunflower, canola, coconut, hemp, palm oil and even algae show promise. The substrate can be of crude or water degummed quality or further processed (refined, bleached and deodorized). Also animal fats including tallow, lard, poultry, marine oil as well as waste vegetable and animal fats and oil, commonly known as yellow and brown grease can be used. The suitable fats and oils may be pure triglyceride or a mixture of triglyceride and free fatty acids, commonly seen in waste vegetable oil and animal fats. The substrate may also be obtained from vegetable oil deodorizer distillates. The type of fatty acids in the substrate comprises those naturally occurring as glycerides in vegetable and animal fats and oils. These include oleic acid, linoleic acid, linolenic acid, palmetic acid and lauric acid to name a few. Minor constituents in crude vegetable oils are typically phospholipids, free fatty acids and partial glycerides i.e. mono- and diglycerides. When used herein the phrase "fatty acid residues" refers to fatty acids, either free or esterified as in triglycerides, diglycerides, monoglycerides or fatty acid alkyl esters.

The phosphatide content in a crude oil may vary from 0.5-3% w/w corresponding to a phosphorus content in the range of 200-10.000 ppm, more preferably in the range of 250-1200 ppm. Apart from the phosphatides the crude oil also contains small concentrations of carbohydrates, sugar compounds and metal/phosphatide acid complexes of Ca, Mg and Fe.

Biodiesel Fatty acid alkyl esters, such as fatty acid methyl esters (FAME) and fatty acid ethyl esters are also called biodiesel, because they are used as an additive to fossil diesel. Biodiesel constitutes an increasingly important additive or substitute for diesel fuels based on fossil oil because it is produced from renewable resources.

Alcohol The alcohol used in the method of the invention is preferably a lower alcohol having 1 to 5 carbon atoms ($C_1$-$C_5$). Preferred alcohols are methanol and ethanol.

Lipolytic enzyme The lipolytic enzyme of the method of the present invention may be one selected from the group consisting of lipolytic enzymes and variants of lipolytic enzymes from *Candida Antarctica, Hyphozyma* sp., *Candida parapsilosis, Candida rugosa, Pseudomonas cepacia, Geotricum candidum, Rhizomucor miehei, Crytococcus* spp. S-2, *Candida parapsilosis, Humicola insolens* and *Thermomyces lanuginosus* (formerly *Humicola*). Said lipolytic enzyme includes lipases, cutinases and acyl-transferases and may be 60% identical with a lipolytic enzyme selected from the group consisting of the above mentioned species. Preferably, the lipolytic enzyme of the method of the present invention is 70% identical with a lipolytic enzyme selected from the group consisting of the above mentioned species, more preferably 75% identical, more preferably 80% identical, more preferably 85% identical, more preferably 90% identical, more preferably 95% identical, even more preferably 97 or 98% identical or most preferably 99% identical with a lipolytic enzyme selected from the group consisting of the above mentioned species. Preferred lipolytic enzymes are *Thermomyces lanuginosus* (formerly *Humicola*) lipase variants according to WO 00/60063, the parent *Thermomyces lanuginosus* lipase and *Candida antarctica* Lipase B.

In another aspect, the present invention includes two different lipolytic enzymes, wherein the first lipolytic enzyme is characterised in that it exhibits higher activity against triglyceride than free fatty acids, whereas the second lipolytic enzyme exhibits higher activity against free fatty acids than triglyceride. Accordingly, the first lipolytic enzyme is defined as one having a ratio of activity on triglyceride (measured as conversion of triglyceride to fatty acid alkyl esters) to activity on FFA (measured as conversion of FFA to fatty acid alkyl esters) below 0.2. The second lipolytic enzyme is defined as one having a ratio of activity on triglyceride (measured as conversion of triglyceride to fatty acid alkyl esters) to activity on FFA (measured as conversion of FFA to fatty acid alkyl esters) above 0.5.

Phospholipases Preferably, a phospholipase (PL) used in the method of the invention is a phospholipase obtained from a microorganism, preferably a filamentous fungus, a yeast, or a bacterium and selected from the phospholipase types $A_1$, $A_2$, B and lyso-phospholipases For the purpose of the present invention the term "obtained from", as used herein in connection with a specific microbial source, means that the enzyme and consequently the DNA sequence encoding said enzyme is produced by the specific source.

The enzyme is then obtained from said specific source by standard known methods enabling the skilled person to obtain a sample comprising the enzyme and capable of being used in a process of the invention. Said standard methods may be direct purification from said specific source or cloning of a DNA sequence encoding the enzyme followed by recombinant expression either in the same source (homologous recombinant expression) or in a different source (heterologous recombinant expression).

More preferably, a phospholipase used in a process of the invention is obtained from a filamentous fungal species within the genus *Fusarium*, such as a strain of *F. culmorum, F. heterosporum, F. solani*, or in particular a strain of *F. oxysporum*; or a filamentous fungal species within the genus *Aspergillus*, such as a strain of *Aspergillus awamori, Aspergillus foetidus, Aspergillus japonicus, Aspergillus niger* or in particular *Aspergillus oryzae*.

Examples of suitable *Fusarium* phospholipases are disclosed in:
1) Tsung-Che et al. (Phytopathological notes 58:1437-38 (1968)) (a phospholipase from *Fusarium solani*); and
2) EP Patent Application No. 97610056.0 disclosing a suitable *F. culmorum* PL (see example 18 in said doc.) and a suitable *F. oxysporum* PL (see example 1-17).

Suitable *Aspergillus* phospholipases are diclosed in
3) EP 575133 disclosing numerous different *Aspergillus* PL's (see claim 14) and in particular a PL from *A. oryzae* (claim 17 or 18) and a PL from *A. niger* (claim 19); and
4) DE 19527274 A1 dicloses a suitable *Aspergillus* preparation (see examples).
Further the commercial available phospholipase preparation Degomma VOD (Roehm, Germany), which is believed to comprise an *Aspergillus* phospholipase is suitable to be used in a process of the invention. Preferred phospholipases are *Thermomyces lanuginosus* phospholipase variants as disclosed in WO 00/32758, Example 5 and the commercial product Lecitase® Ultra (Novozymes A/S, Denmark).

The enzymes may be applied as lyophilised powder, immobilised or in aqueous solution.

For purposes of the present invention, the degree of identity may be suitably determined according to the method described in Needleman, S. B. and Wunsch, C. D., (1970), Journal of Molecular Biology, 48, 443-45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version 8, August 1994, Genetics Computer Group, 575 Science Drive, Madison, Wis., USA 53711).

Two given sequences can be aligned according to the method described in Needleman (supra) using the same parameters. This may be done by means of the GAP program (supra).

Further, the invention relates to a batch process and/or a continuous, staged process to produce fatty acid alkyl esters using a first and a second lipolytic enzyme as described above, wherein the alcohol is added continuously or stepwise, and wherein the enzymes are recycled or used only once. If the enzymes are in an aqueous phase, this phase can be separated from the fatty phase by a decanter, a settler or by centrifugation. In the continuously process the two phases, oil and aqueous, respectively, can be processed counter-currently. Kosugi, Y; Tanaka, H. and Tomizuka, (1990), Biotechnology and Bioengineering, vol. 36, 617-622, describes a continuous, counter-current process to hydrolyse vegetable oil by immobilized lipase.

General Description of Preparation of Phosphorous Reduced Fatty Acid Alkyl Esters The substrate comprising triglyceride and/or fatty acids is mixed with alcohol, preferably methanol or ethanol and heated to 30-70° C., preferably app. 50° C. on a reciprocal water shaking bath (200 rpm). Preferably water is added and the solution is mixed and further heated to the desired temperature. The enzymes are added and the solution is mixed vigorously and left on reciprocal water shaking bath at the desired temperature, preferably 50° C. and 200 rpm to react. The phases of the reaction mixture can be mixed by the use of high shear mixers, such as types from Silverson or IKA Labortechnik, as used in enzymatic degumming of vegetable oil (Clausen, K. (2001), European Journal of Lipid Science and Technology, vol. 103, 333-340).

Typically enzymatic degumming takes place at pH 3-7. In order to optimize the process, the pH often needs to be adjusted to fit the other conditions of the process, including the type of substrate and the concentration of chelating agents. Preferably the pH is 4-5.

The [methanol]/[fatty acid residue] molar ratio should be at least 0.1 and maximum 10, preferable in the range 0.3-5, more preferable 0.4-2. The alcohol can be added stepwise to the reaction over time. Water can be added separately or within an aqueous enzyme solution. The final concentration of water in the reaction mixture can be 0-50% (w/w), preferably 5-40%, more preferably 5-30%. The substrate comprises 1-99% (w/w) triglyceride, preferably in the range of 70-95%. Further, the substrate may comprise free fatty acids amounting to 0.01-95% (w/w), preferably in the range of 0.01-30%. Also, mono- and diglycerides and phospholipids may be present.

The course of the reaction can be followed by withdrawing samples from the reaction mixture after a certain period of reaction time. The samples are centrifuged for 14 minutes at 14000 rpm. The upper layer consists of fatty material not soluble in the water phase and this is analyzed by $^1$H NMR (using $CDCl_3$ as solvent). The enzymatic treatment is followed by separation of the aqueous phase and the oil phase. This separation may be performed by conventional means, e.g. centrifugation, decanting or settlers.

The amount of lipolytic enzyme added can be determined in terms of lipolytic activity on tributyrin (LU). A substrate for lipolytic enzymes is prepared by emulsifying tributyrin (glycerin tributyrate) using gum Arabic as emulsifier. The hydrolysis of tributyrin at 30° C. at pH 7 is followed in a pH-stat titration experiment. One unit of lipase activity (1

LU) equals the amount of enzyme capable of releasing 1 µmol butyric acid/min at the standard conditions.

The phosphor content in the fatty phase after 24 hrs. reaction time is determined as described by Clausen, K. Eur. J. Lipid Sci. Technol. 103 (2001), 333-340.

The method of the present invention may be further optimized by addition of chelating agents, which chelates metal components in the reaction mixture and thereby increase the amount of hydratable phospholipids in the water phase. Chelating agents such as citric acid or ethylenediaminetetraaceticacid (EDTA) may be added in the range of 0.01-1% w/w based on the oil content. Preferred amounts are 0.04-0.1%.

After removal of the phosphorous containing compounds from the discharged water phase, the enzymes present in the water phase may be fully or partially recycled by backmixing the water phase into the reaction mixture including new substrate.

The content of the phosphorous containing components in the fatty phase of the reaction mixture may be further reduced by treatment with silica, which absorbs phospholipids among others.

Cloning a DNA Sequence Encoding a Lipolytic Enzyme or a Phospholipase

The DNA sequence encoding a parent lipolytic enzyme or phospholipase may be isolated from any cell or microorganism producing the enzyme in question, using various methods well known in the art. First, a genomic DNA and/or cDNA library should be constructed using chromosomal DNA or messenger RNA from the organism that produces the enzyme to be studied. Then, if the amino acid sequence of the lipolytic enzyme or phospholipase is known, labelled oligonucleotide probes may be synthesized and used to identify lipolytic or phospholipase enzyme-encoding clones from a genomic library prepared from the organism in question. Alternatively, a labelled oligonucleotide probe containing sequences homologous to another known lipolytic or phospholipase enzyme genes could be used as a probe to identify relevant enzyme-encoding clones, using hybridization and washing conditions of lower stringency.

Yet another method for identifying lipolytic or phospholipase enzyme-encoding clones would involve inserting fragments of genomic DNA into an expression vector, such as a plasmid, transforming cutinase-negative bacteria with the resulting genomic DNA library, and then plating the transformed bacteria onto agar containing a substrate for lipolytic or phospholipase enzymes (i.e. triglyceride), thereby allowing clones expressing the lipolytic enzyme to be identified.

Alternatively, the DNA sequence encoding the enzyme may be prepared synthetically by established standard methods, e.g. the phosphoroamidite method described by S. L. Beaucage and M. H. Caruthers, (1981), Tetrahedron Letters 22, p. 1859-1869, or the method described by Matthes et al., (1984), EMBO J. 3, p. 801-805. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487-491.

Expression Vector

The recombinant expression vector carrying the DNA sequence encoding a lipolytic enzyme or phospholipase of the method of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

The expression vector of the invention may also comprise a suitable transcription terminator and, in eukaryotes, polyadenylation sequences operably connected to the DNA sequence encoding the lipolytic or phospholipase enzyme of the method of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a cutinase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a lipolytic or phospholipase enzyme, especially in a bacterial host, are the promoter of the lac operon of *E. coli*, the *Streptomyces coelicolor* agarase gene dagA promoters, the promoters of the *Bacillus licheniformis* alfa-amylase gene (amyL), the promoters of the *Bacillus stearothermophilus* maltogenic amylase gene (amyM), the promoters of the *Bacillus amyloliquefaciens* alfa-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419-434, *Rhizomucor miehei* aspartic proteinase, *A. niger* neutral alfa-amylase, *A. niger* acid stable alfa-amylase, *A. niger* glucoamylase, *Rhizomucor miehei* lipase, *A. oryzae* alkaline protease, *A. oryzae* triose phosphate isomerase, or *A. nidulans* acetamidase.

Host Cells

A host cell for production of the enzymes used in the method of invention, either comprising a DNA construct or an expression vector of the invention as defined above, is advantageously used as a host cell in the recombinant production of a lipolytic or phospholipase enzyme. The cell may be transformed with a DNA construct encoding a lipolytic or phospholipase enzyme, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be trans-formed with an expression vector as described above in connection with the different types of host cells.

The host cell may be a cell of a higher organism such as a mammal or an insect, particularly a microbial cell, e.g. a bacterial or a fungal (including yeast) cell.

Examples of suitable bacteria are Gram positive bacteria such as *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, or *Streptomyces lividans* or *Streptomyces murinus*, or gram negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*.

The host cell may also be a filamentous fungus e.g. a strain belonging to a species of *Aspergillus*, particularly *Aspergillus oryzae* or *Aspergillus niger*, or a strain of Fusarium, such as a strain of *Fusarium oxysporum*, *Fusarium graminearum* (in the perfect state named *Gibberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides*, *Fusarium bactridioides*, *Fusarium sambucinum*, *Fusarium roseum*, and *Fusarium roseum* var. *graminearum*), *Fusarium cerealis* (synonym with *Fusarium crokkwellense*), or *Fusarium venenatum*.

In a particular embodiment the host cell is a protease deficient or protease minus strain. This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host microorganism is described in EP 238 023 (Novo Nordisk A/S), the contents of which are hereby incorporated by reference.

Production of Lipolytic or Phospholipase Enzymes by Cultivation of Transformant

The enzymes used in the method of the invention may be produced by a method comprising cultivating a host cell under conditions conducive to the production of the enzymes and recovering the enzymes from the cells and/or culture medium.

The medium used to cultivate the cells may be any conventional medium suitable for growing the host cell in question and obtaining expression of the lipolytic enzyme of the invention. Suitable media are available from commercial suppliers or may be prepared according to published recipes (e.g. as described in catalogues of the American Type Culture Collection).

The lipolytic or phospholipase enzyme secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

EXAMPLE

Transesterification and Degumming of Crude Rape Seed Oil

Formation of phosphorous reduced fatty acid methyl esters from crude rape seed oil by use of a lipolytic enzyme and a phospholipase.

Lipolytic enzyme: *Thermomyces lanuginosus* lipase variant according to WO 00/60063, dosing: 4000 LU/8 gram oil. Phospholipase: *Thermomyces lanuginosus* phospholipase variant according to WO 00/32758, Example 5 (activity 10.000 LU/g), dosing: 30 ppm or 100 ppm. (corresponding to 300 and 1000 LU/kg oil, respectively). Substrate: 100% crude rape seed oil, 8 grams. Methanol content: 1.5 molar equivalents based on oil, 1.72 ml. 30% $H_2O$ based on oil weight. Sampling time: 3 and 24 hours. Reaction temperature: 50° C.

The substrate-methanol mixture is heated to 50° C. on a reciprocal water shaking bath (200 rpm). Demineralised water is added (volume depending on added enzyme volume; total amount of water: 2.40 ml including water from enzyme addition), corresponding to 30 w/w % of the oil. The mixture is heated to 50° C. Then enzymes (lipase and phospholipase) are added to the mixture and mixed on an high shear mixer (Ultra Turrax® T25, IKA Janke and Kunkel, Germany) for 30 seconds, and left in a shaking water bath for 24 hours (reciprocal shaking, 50° C. and 200 rpm).

Samples are withdrawn from the reaction mixture after 3 and 24 hours reaction time, respectively and centrifuged for 14 minutes at 14000 rpm. The upper layer consists of fatty material not soluble in the water phase and this is analyzed by $^1$H NMR (using $CDCl_3$ as solvent) Varian 400 MHz spectrometer (Varian Inc. CA, USA). The conversion of the fatty acids residues into fatty acid methyl ester is determined by the ratio of the methyl signals from the fatty acid methyl esters, —$COOCH_3$ (3.70 ppm) and $CH_3CH_2$— (1.0-0.9 ppm) from the fatty acid residues.

No formation of methyl ester was found the experiments without lipase and phospholipase nor in experiments with only phospholipase. The phosphor content in the fatty phase after 24 hrs. reaction time was determined as described by Clausen, K. Eur. J. Lipid Sci. Technol. 103 (2001), 333-340.

TABLE 1

Phosphorous content and methyl ester formation after enzymatic treatment

| Enzymes in mixture | Mol % methyl ester conversion 24(3) hrs | P-value (ppm) after 24 hours reaction time |
|---|---|---|
| Lipase (4000 LU) + 30 ppm phospholipase | 94(60) | 26 |
| Lipase (4000 LU) + 30 ppm phospholipase | 93(59) | 22 |

TABLE 1-continued

Phosphorous content and methyl ester formation after enzymatic treatment

| Enzymes in mixture | Mol % methyl ester conversion 24(3) hrs | P-value (ppm) after 24 hours reaction time |
|---|---|---|
| Lipase (4000 LU) + 100 ppm phospholipase | 86(52) | 12 |
| Lipase (4000 LU) + 100 ppm phospholipase | 94(62) | 17 |
| No enzymes | 0 | 74 |
| No enzymes | 0 | 75 |

It is evident that the combination of a lipolytic enzyme and a phospholipase results in high conversion of triglyceride to methyl esters and a low content of phosphorous-containing components in a one step method.

The invention claimed is:

1. A method for producing a reduced-phosphorous content fatty acid alkyl ester comprising:
   mixing an alcohol, a substrate comprising triglyceride and/or fatty acids, one or more lipolytic enzymes, one or more phospholipases and water to form a reaction mixture with two phases,
   recovering the reduced-phosphorous content fatty acid alkyl ester.

2. The method of claim 1, wherein the phosphorous content of the fatty acid alkyl esters is reduced to not more than 50 ppm.

3. The method of claim 1, wherein the substrate further comprises free fatty acids.

4. The method of claim 1, wherein the triglyceride is derived from one or more of vegetable oil feedstock, rapeseed oil, soybean oil, mustard oil, sunflower oil, canola oil, coconut oil, hemp oil, palm oil, tall oil, animal fats including tallow, lard, poultry and fish oil.

5. The method of claim 4, wherein a chelating agent is added in the range of 0.01-10;% w/w based on the oil content.

6. The method of claim 1, wherein the molar ratio between alcohol and fatty acid residues is least 0.1 and maximum 10.

7. The method of claim 1, wherein the alcohol is methanol or ethanol.

8. The method of claim 1, wherein the reaction mixture comprises water up to 50% (w/w).

9. The method of claim 1, wherein the temperature is 30-70° C.

10. The method of claim 1, wherein the lipolytic enzyme is 60% identical with a lipolytic enzyme selected from the group consisting of lipolytic enzymes from *Candida antarctica, Candida parapsilosis, Candida rugosa, Crytococcus* spp. S-2, *Geotricum candidum, Hyphozyma* sp., *Pseudamonas cepacia, Rhizomucor miehei*, and *Thermomyces lanuginasus*.

11. The method of claim 1, wherein the phospholipase is 60% identical with a phospholipase selected from the group consisting of phospholipases from *Aspergillus, Fusarium*, and *Thermomyces*.

12. The method of claim 11, wherein the phospholipase is selected from the group consisting of phospholipases from a strain of *Aspergillus awamori, Aspergillus foetidus, Aspergillus japonicus, Aspergillus niger, Aspergillus oryzae, Fusarium culmorum, Fusanum heterosporum, Fusarium oxysporum, Fusarium solani*, and *Thermomyces lanuginosus*.

13. The method of claim 1, wherein the process is proceeding in a batch mode.

14. The method of claim 1, wherein the process is proceeding in a continuous mode.

15. The method of claim 1, wherein solution phases in the reaction mixture are mixed using a high shear mixer.

16. The method of claim 1, wherein the process is conducted in a counter-current mode.

17. The method of claim 1, wherein the water phase including enzymes is recycled fully or partially into the reaction mixture, which mixture also contains new substrate.

* * * * *

UNITED STATES PATENT AND TRADEMARK OFFICE
CERTIFICATE OF CORRECTION

| | | |
|---|---|---|
| PATENT NO. | : 8,012,724 B2 | Page 1 of 1 |
| APPLICATION NO. | : 11/916052 | |
| DATED | : September 6, 2011 | |
| INVENTOR(S) | : Holm et al. | |

It is certified that error appears in the above-identified patent and that said Letters Patent is hereby corrected as shown below:

In the claims section:

col. 11, line 23, delete "phospholipases" and insert -- phospholipase enzymes -- col. 11, line 38, delete "0.01-10;% w/w" and insert -- 0.01-1% w/w -- col. 12, line 24, delete "*Fusanum*" and insert -- *Fusarium* --

Signed and Sealed this
Twenty-first Day of February, 2012

David J. Kappos
*Director of the United States Patent and Trademark Office*